United States Patent
Wang et al.

(10) Patent No.: US 8,103,458 B2
(45) Date of Patent: Jan. 24, 2012

(54) EXHAUST GAS SENSING SYSTEM AND METHOD FOR DETERMINING CONCENTRATIONS OF EXHAUST GAS CONSTITUENTS

(75) Inventors: Da Yu Wang, Troy, MI (US); Sheng Yao, Macomb, MI (US); David D. Cabush, Kokomo, IN (US); Walter T. Symons, Grand Blanc, MI (US); Robert J. Farhat, Grosse Pointe Woods, MI (US)

(73) Assignee: Delphi Technologies, Inc., Troy, MI (US)

( * ) Notice: Subject to any disclaimer, the term of this patent is extended or adjusted under 35 U.S.C. 154(b) by 478 days.

(21) Appl. No.: 12/337,784

(22) Filed: Dec. 18, 2008

(65) Prior Publication Data

US 2010/0161242 A1   Jun. 24, 2010

(51) Int. Cl.
   *G01N 31/00* (2006.01)
   *G01N 33/497* (2006.01)
(52) U.S. Cl. .......................................... 702/24; 73/23.31
(58) Field of Classification Search .................... 702/24, 702/22; 73/23.31, 23.32; 204/424, 431
   See application file for complete search history.

(56) References Cited

U.S. PATENT DOCUMENTS

| | | |
|---|---|---|
| 4,770,760 A | 9/1988 | Noda et al. |
| 4,927,517 A | 5/1990 | Mizutani et al. |
| 5,145,566 A | 9/1992 | Logothetis et al. |
| 6,153,071 A | 11/2000 | Omara et al. |
| 6,224,727 B1 | 5/2001 | Miyata et al. |
| 6,254,750 B1 * | 7/2001 | Patrick et al. .................. 204/425 |
| 6,544,405 B2 | 4/2003 | Clyde et al. |
| 6,555,159 B2 | 4/2003 | Clyde et al. |
| 6,689,266 B2 | 2/2004 | Kato et al. |
| 7,074,319 B2 | 7/2006 | Wang et al. |
| 7,294,252 B2 | 11/2007 | Wang et al. |
| 7,422,052 B2 | 9/2008 | Reyzin et al. |
| 2007/0079597 A1 | 4/2007 | Wang et al. |
| 2007/0080074 A1 | 4/2007 | Wang et al. |
| 2007/0100995 A1 | 5/2007 | Isenmann et al. |
| 2008/0230385 A1 | 9/2008 | Lankheet et al. |
| 2010/0077833 A1 * | 4/2010 | Wang et al. ................... 73/23.31 |

FOREIGN PATENT DOCUMENTS

DE   10027900 A1   12/2001
WO   WO2007014388   2/2007

OTHER PUBLICATIONS

David B. Quinn, Earl W. Lankheet, Kenneth Howden, NOx Sensor for Direct Injection Emission Control, Combustion and Emission Control for Advanced CIDI Engines FY 2002 Progress Report, 93-97.

(Continued)

*Primary Examiner* — Bryan Bui
(74) *Attorney, Agent, or Firm* — Mark H. Svoboda (57) ABSTRACT

An exhaust gas sensing system and a method for determining concentrations of exhaust gas constituents are provided. The exhaust gas sensing system includes a $NH_3$ sensing cell, a $NO_2$ sensing cell, a $NO_x$ pumping cell, and a current sensor that detects an electrical current flowing through the $NO_x$ pumping cell. A computer determines a $NO_2$ concentration value, a $NH_3$ concentration value, a NO concentration value, and a $NO_x$ concentration value based on signals from the $NH_3$ sensing cell, the $NO_2$ sensing cell, and the current sensor.

4 Claims, 6 Drawing Sheets

OTHER PUBLICATIONS

David B. Quinn, Earl W. Lankheet, Roland Gravel, NOx Sensor for Direct Injection Emission Control, Advanced Combustion Engine R&D FY 2003 Progress Report, 159-164.

Michael Pollard, Craig Habeger, Paul Park, Amy Fluharty, John Fairbanks, Development of Metal Substrate for DeNOx Catalysts and Particulate Traps, Advanced Combustion Engine R&D FY 2004 Progress Report, 229-256.

David B. Quinn, Earl W. Lankheet, Roland Gravel, NOx Sensor for Direct Injection Emission Control, Advanced Combustion Engine Technologies FY 2005 Progress Report, 243-258.

U.S. Appl. No. 11/839,340, filed Aug. 15, 2007 entitled: Oxygen Sensor and Method for Manufacturing the Oxygen Sensor.

U.S. Appl. No. 12/056,789, filed Mar. 27, 2008 entitled: Exhaust Gas Sensing System and Methods for Sensing Concentrations of Exhaust Gas Constituents.

U.S. Appl. No. 12/109,405, filed Apr. 25, 2008 entitled: Systems and Methods for Sensing an Ammonia Concentration in Exhaust Gases.

U.S. Appl. No. 12/240,354, filed Sep. 29, 2008 entitled: Exhaust Gas Sensor and Method for Determining Concentrations of Exhaust Gas Constituents.

* cited by examiner

EXHAUST GAS SENSING SYSTEM AND METHOD FOR DETERMINING CONCENTRATIONS OF EXHAUST GAS CONSTITUENTS

BACKGROUND

A nitrogen oxides ($NO_x$) sensor has been developed that detects $NO_x$ concentrations. However, the $NO_x$ sensor is not capable of directly determining nitrogen dioxide ($NO_2$) concentrations. Further, the $NO_x$ sensor may not be able to determine $NO_x$ concentrations in exhaust gases when the exhaust gases have ammonia ($NH_3$) therein.

Accordingly, the inventors herein have recognized a need for an improved exhaust gas sensor that minimizes and/or eliminates the above-mentioned deficiencies.

SUMMARY OF THE INVENTION

An exhaust gas sensing system in accordance with an exemplary embodiment is provided. The exhaust gas sensing system includes a $NH_3$ sensing cell configured to generate a first voltage indicative of a combination of a $NH_3$ concentration and a $NO_2$ concentration in exhaust gases communicating with the $NH_3$ sensing cell. The exhaust gas sensing system further includes a $NO_2$ sensing cell configured to generate a second voltage indicative of a $NO_2$ concentration in exhaust gases communicating with the $NO_2$ sensing cell. The exhaust gas sensing system further includes a $NO_x$ pumping cell configured to generate an electrical current indicative of combination of a NO concentration, a $NO_2$ concentration, and a $NH_3$ concentration in exhaust gases communicating with the $NO_x$ pumping cell. The exhaust gas sensing system further includes a current sensor configured to measure the electrical current flowing through the $NO_x$ pumping cell and to output a current measurement signal indicative of a magnitude of the electrical current. The exhaust gas sensing system further includes a computer configured to receive the first voltage, the second voltage, and the current measurement signal. The computer is further configured to determine a $NO_2$ concentration value indicative of the $NO_2$ concentration in the exhaust gases communicating with the $NO_2$ sensing cell based on the second voltage. The computer is further configured to determine a $NH_3$ concentration value indicative of the $NH_3$ concentration in the exhaust gases communicating with the $NH_3$ sensing cell based on the first voltage and the $NO_2$ concentration value. The computer is further configured to determine a nitrogen monoxide (NO) concentration value indicative of a NO concentration in the exhaust gases communicating with the $NO_x$ pumping cell based on the current measurement signal, the $NO_2$ concentration value, and the $NH_3$ concentration value. The computer is further configured to determine a $NO_x$ concentration value based on the NO concentration value and the $NO_2$ concentration value. The computer is further configured to store the $NO_2$ concentration value, the $NH_3$ concentration value, the NO concentration value, and the $NO_x$ concentration value in a memory device.

A method for determining concentrations of exhaust gas constituents in accordance with another exemplary embodiment is provided. The method includes generating a first voltage utilizing a $NH_3$ sensing cell that is indicative of a combination of a $NH_3$ concentration and a $NO_2$ concentration in exhaust gases communicating with the $NH_3$ sensing cell. The method further includes generating a second voltage utilizing a $NO_2$ sensing cell that is indicative of a $NO_2$ concentration in exhaust gases communicating with the $NO_2$ sensing cell. The method further includes generating an electrical current utilizing a $NO_x$ pumping cell that is indicative of combination of a NO concentration, a $NO_2$ concentration, and a $NH_3$ concentration in exhaust gases communicating with the $NO_x$ pumping cell. The method further includes measuring the electrical current flowing through the $NO_x$ pumping cell utilizing a current sensor and outputting a current measurement signal from the current sensor indicative of a magnitude of the electrical current. The method further includes receiving the first voltage, the second voltage, and the current measurement signal at a computer. The method further includes determining a $NO_2$ concentration value indicative of the $NO_2$ concentration in the exhaust gases communicating with the $NO_2$ sensing cell based on the second voltage, utilizing the computer. The method further includes determining a $NH_3$ concentration value indicative of the $NH_3$ concentration in the exhaust gases communicating with the $NH_3$ sensing cell based on the first voltage and the $NO_2$ concentration value, utilizing the computer. The method further includes determining a NO concentration value indicative of a NO concentration in the exhaust gases communicating with the $NO_x$ pumping cell based on the current measurement signal, the $NO_2$ concentration value, and the $NH_3$ concentration value, utilizing the computer. The method further includes determining a $NO_x$ concentration value based on the NO concentration value and the $NO_2$ concentration value, utilizing the computer. The method further includes storing the $NO_2$ concentration value, the $NH_3$ concentration value, the NO concentration value, and the $NO_x$ concentration value in a memory device, utilizing the computer.

DETAILED DESCRIPTION OF EXEMPLARY EMBODIMENTS

Figure 1:
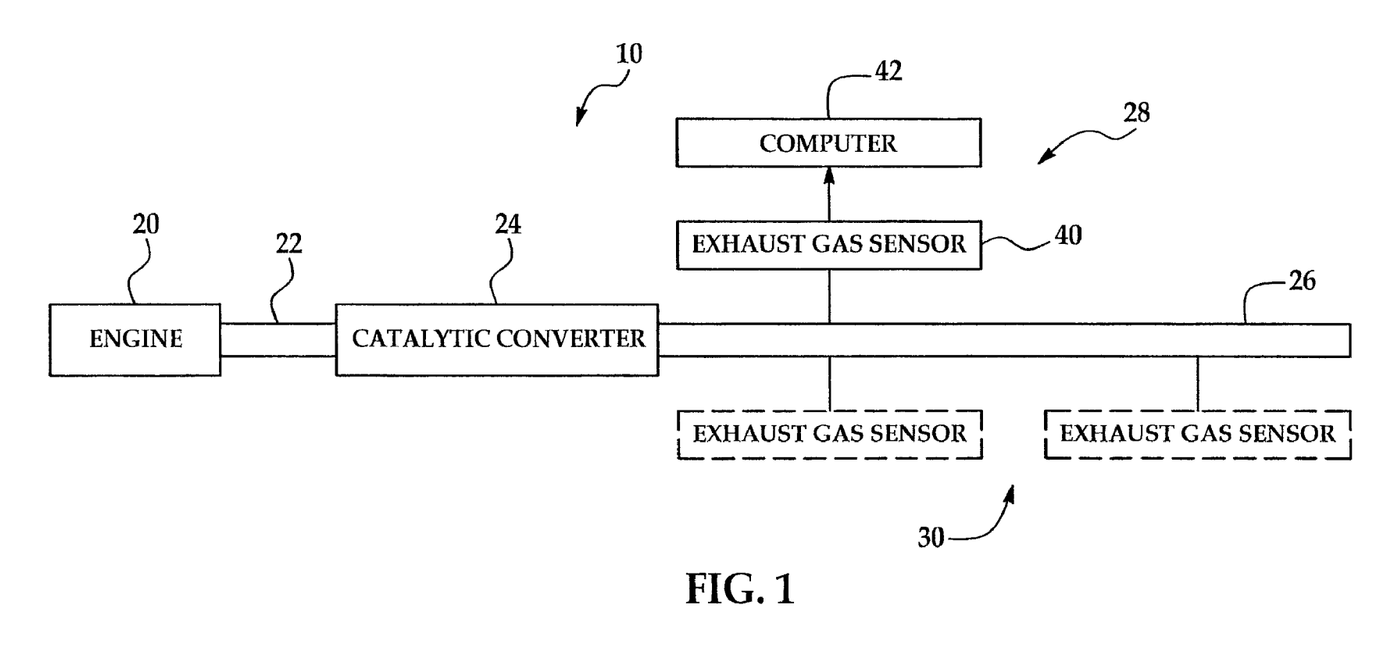
FIG. 1 is a schematic of a vehicle having first and second exhaust gas sensing systems in accordance with exemplary embodiments.

Referring to FIG. 1, a vehicle 10 is illustrated. The vehicle 10 includes an engine 20, an exhaust pipe 22, a catalytic converter 24, an exhaust pipe 26, and exhaust gas sensing systems 28, 30. The engine 20 emits exhaust gases that are routed through the exhaust pipe 22 and the catalytic converter 24 to the exhaust pipe 26. The exhaust gas sensing systems 28, 30 communicate with the exhaust pipe 26 to determine concentrations of exhaust gas constituents in the exhaust gases. In particular, the exhaust gas sensing systems 28, 30 can accurately determine a $NO_2$ concentration, a $NH_3$ concentration, a NO concentration, and a $NO_x$ concentration in the exhaust gases. The sensors of the exhaust gas sensing systems 28 and 30 can also be positioned in other parts of the exhaust system. For example, the sensors can be positioned immediately downstream of the engine 20 but upstream of the catalytic converter 24, or inside the catalytic converter 24.

Figure 2:
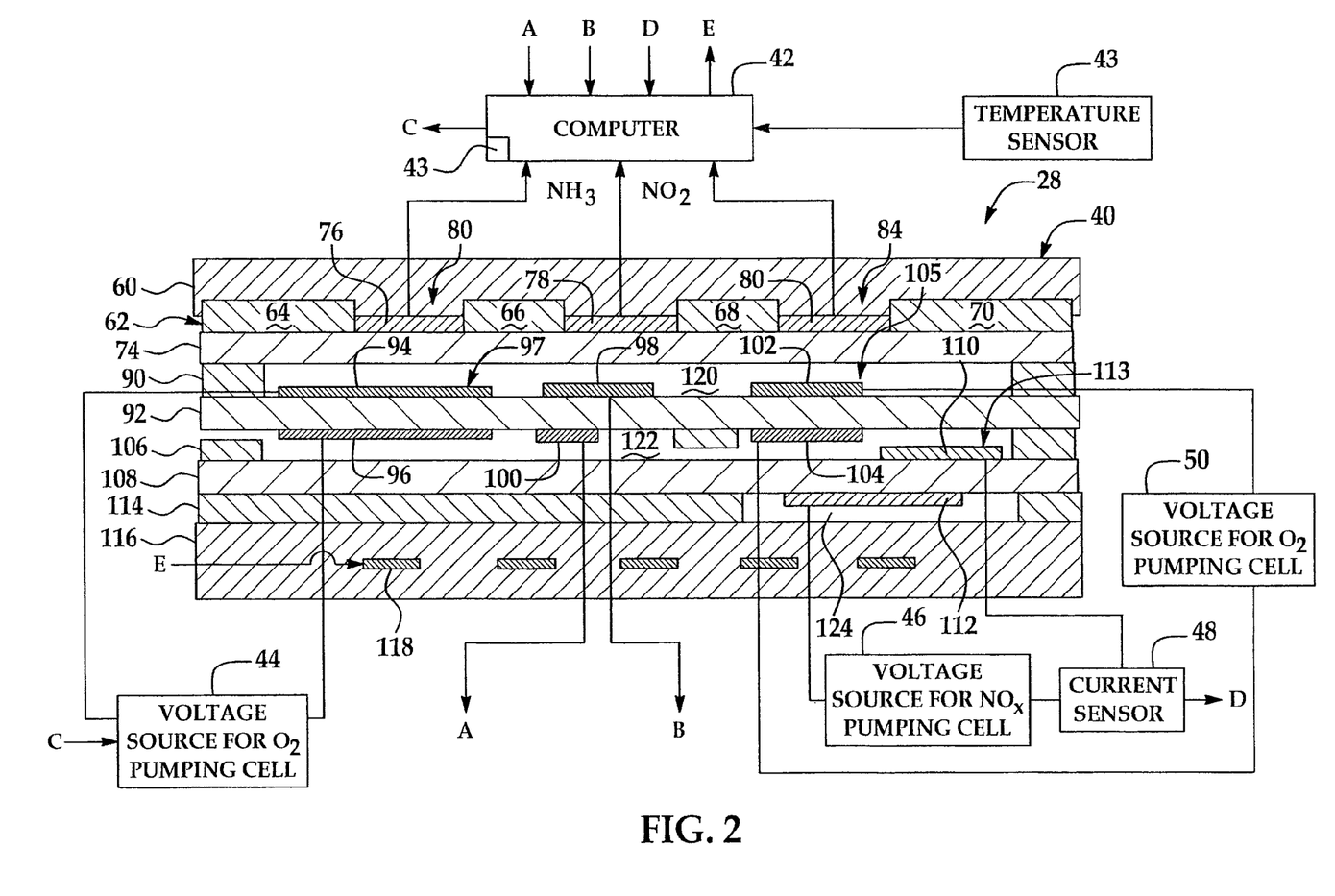
FIG. 2 is a schematic of the first exhaust gas sensing system of FIG. 1.

Referring to FIG. 2, the exhaust gas sensing system 28 includes an exhaust gas sensor 40, a temperature sensor 43, a voltage source 44, a voltage source 46, a current sensor 48, and a voltage source 50.

The exhaust gas sensor 40 communicates with the exhaust gases in the exhaust pipe 26 to generate signals that are either directly or indirectly indicative of concentrations of $NO_2$, $NH_3$, NO, and $NO_x$ in the exhaust gases in the exhaust pipe 26. The exhaust gas sensor 40 includes a porous protection layer 60, an alumina layer 62, a zirconia layer 74, a $NH_3$ sensing electrode 76, a reference electrode 78, a $NO_2$ sensing electrode 80, an alumina layer 90, a zirconia layer 92, pump electrodes 94, 96, an $O_2$ reference electrode 98, an oxygen sensing electrode 100, pump electrodes 102, 104, an alumina layer 106, a zirconia layer 108, a $NO_2$ sensing electrode 80, a $NO_x$ sensing electrode 110, a reference electrode 112, alumina layers 114, 116, and a heater coil 118.

The porous protection layer 60 is configured to allow exhaust gases to diffuse therethrough to contact the $NH_3$ sensing electrode 76, the reference electrode 78, and the $NO_2$ sensing electrode 80. In one exemplary embodiment, the porous protection layer 60 is constructed from porous alumina. As shown, the layer 60 is disposed at least in part on a first side of the alumina layer 62.

A second side of the alumina layer 62 is disposed on a first side of the zirconia layer 74. The alumina layer 62 includes portions 64, 66, 68, 70 disposed apart from one another that form gaps therebetween. The $NH_3$ sensing electrode 76 is disposed in a gap between the portions 64, 66 of the alumina layer 62 and is further disposed between the layer 60 and the zirconia layer 74. In one exemplary embodiment, the $NH_3$ sensing electrode 76 is constructed of $BiVO_4$ doped with 0-20 mole % of MgO, 0-10 mole % of $B2O_3$, 0-10 mole % of SrO. Further, in one exemplary embodiment, the zirconia layer 74 is an oxide ion conducting solid electrolyte constructed of partially yttria-doped zirconia.

The reference electrode 78 is disposed in a gap between the portions 66, 68 of the alumina layer 62 and is further disposed between the layer 60 and the zirconia layer 74. In one exemplary embodiment, the reference electrode 78 is constructed of a platinum-gold (Pt—Au) alloy.

The $NO_2$ sensing electrode 80 is disposed in a gap between the portions 68, 70 of the alumina layer 62 and is further disposed between the layer 60 and the zirconia layer 74. In one exemplary embodiment, the $NO_2$ sensing electrode is constructed of $BaFe_{12}O_{19}$ doped with 0-20 mole % of BaO, 0-20 mole % of (MgO, NiO, ZnO).

The combination of the $NH_3$ sensing electrode 76, the zirconia layer 74, and the reference electrode 78 form a $NH_3$ sensing cell 82 (e.g., $NH_3$ sensing Nernst cell) that generates a voltage indicative of a $NH_3$ concentration in exhaust gases communicating with the $NH_3$ sensing electrode 76, that is received by the computer 42.

The combination of the $NO_2$ sensing electrode 80, the zirconia layer 74, and the reference electrode 78 form a $NO_2$ sensing cell 84 (e.g., $NO_2$ sensing Nernst cell) that generates a voltage indicative of a $NO_2$ concentration in exhaust gases communicating with the $NO_2$ sensing electrode 80, that is received by the computer 42.

The alumina layer 90 is disposed between a second side of the zirconia layer 74 and a first side of the zirconia layer 92. A chamber 120 is formed in the alumina layer 90, which is communicated with ambient air by an air duct running through the sensing element.

The pumping electrode 94 is disposed on a first side of the zirconia layer 92 and the pumping electrode 96 is disposed on a second side of the zirconia layer 92 proximate to the pumping electrode 94. The pumping electrodes 94, 96 are further electrically coupled to the voltage source 44. In one exemplary embodiment, the pumping electrodes 94, 96 are constructed of a Pt—Au alloy.

The combination of the voltage source 44, the electrodes 94, 96 and the zirconia layer 92 comprise an electrochemical pumping cell 97. The pumping cell 97 reduces an amount of oxygen in a first portion of the chamber 122 below a first predetermined oxygen concentration level.

The $O_2$ reference electrode 98 is disposed on the first side of the zirconia layer 92 and the oxygen sensing electrode 100 is disposed on a second side of the zirconia layer 92 proximate to the $O_2$ reference electrode 98. The $O_2$ reference electrode 98 and the oxygen sensing electrode 100 are further electrically coupled to the computer 42. In one exemplary embodiment, the $O_2$ reference electrode 98 and the oxygen sensing electrode 100 are constructed of Pt. A voltage generated between the electrodes 98, 100 is indicative of an oxygen concentration in the chamber 122. The computer 42 measures the voltage between the electrodes 98, 100 indicative of the oxygen concentration, to regulate a voltage output by the voltage source 44 to maintain a concentration of oxygen in a portion of the chamber 122 below a second predetermined oxygen concentration level. The pump current driven between electrodes 94 and 96 is an indication of the oxygen concentration of the exhaust gas.

The pumping electrode 102 is disposed on a first side of the zirconia layer 92 and the pumping electrode 104 is disposed on a second side of the zirconia layer 92 proximate to the pumping electrode 102. The pumping electrodes 102, 104 are further electrically coupled to the voltage source 50. In one exemplary embodiment, the pumping electrodes 102, 104 are constructed of an Pt—Au alloy. The combination of the voltage source 50, the electrodes 102, 104 and the zirconia layer 92 comprise an electrochemical pumping cell 97. The pumping cell 97 reduces an amount of oxygen in a second portion of the chamber 122 below a second predetermined oxygen concentration level.

The alumina layer 106 is disposed between the second side of the zirconia layer 92 and a first side of the zirconia layer 108. A chamber 122 is formed in the alumina layer 106 and fluidly communicates with engine exhaust through a gas-diffusion-limiting aperture extending through a portion of the alumina layer 106. There is a second gas-diffusion-limiting aperture inside chamber 122, which separates the electrodes 96, 100 from the electrodes 104 and 110.

The zirconia layer 108 is disposed between the second side of the alumina layer 106 and a first side of the alumina layer 114. A second side of the alumina layer 114 is disposed on a first side of the alumina layer 116. A chamber 124 is formed in the alumina layer 114. Further, in one exemplary embodiment, the zirconia layer 108 is an oxide ion conducting solid electrolyte constructed of partially yttria-doped zirconia.

The $NO_x$ sensing electrode 110 is disposed on the first side of the zirconia layer 108 fluidly communicates with exhaust gases in the chamber 122. In one exemplary embodiment, the $NO_x$ sensing electrode 110 is constructed of a Pt—Rh alloy. The reference electrode 112 is disposed on the second side of the zirconia layer 108 proximate to the $NO_x$ sensing electrode 110 and fluidly communicates with exhaust gases in the chamber 124. In one exemplary embodiment, the reference electrode 112 is constructed of Pt alloy. The electrodes 110, 112 are electrically coupled to a series combination of the voltage source 46 and the current sensor 48.

The combination of the voltage source 46, the electrodes 110, 112 and the zirconia layer 108 comprise a $NO_x$ electrochemical pumping cell 113 that generates a current indicative of a $NO_x$ concentration in the chamber 122. The current sensor 48 outputs a signal indicative of an amount of electrical current flowing between the electrodes 110, 112, that is received by the computer 42.

The heater coil 118 is disposed in the alumina layer 116. The heater coil 1118 is configured to maintain the exhaust gas sensor 40 within a predetermined temperature range in response to a control signal from the computer 42.

The temperature sensor 43 outputs a signal indicative of a temperature of the exhaust gas sensor 40 that is received by the computer 42. In one exemplary embodiment, the temperature sensor 43 is formed within the exhaust gas sensor 40 and can comprise an impedance circuit that has an impedance that varies proportional to a temperature variation. In another exemplary embodiment, the temperature sensor 43 is a stand-alone temperature sensor that is not part of the exhaust gas sensor 40.

The computer 42 is configured to calculate a $NO_2$ concentration value, a $NH_3$ concentration value, a NO concentration value, and a $NO_x$ concentration value indicative of: a $NO_2$ concentration, a $NH_3$ concentration, a NO concentration, and a $NO_x$ concentration, respectively, in exhaust gases communicating with the exhaust gas sensor 40 based on signals from the exhaust gas sensor 240 and the current sensor 48, as will be described in greater detail below. As shown, the computer 42 is electrically coupled to the voltage source 44, the $NH_3$ sensing electrode 76, the reference electrode 78, the $NO_2$ sensing electrode 80, the $O_2$ reference electrode 98, the oxygen sensing electrode 100, the current sensor 48, and the heater coil 118.

Figure 3:
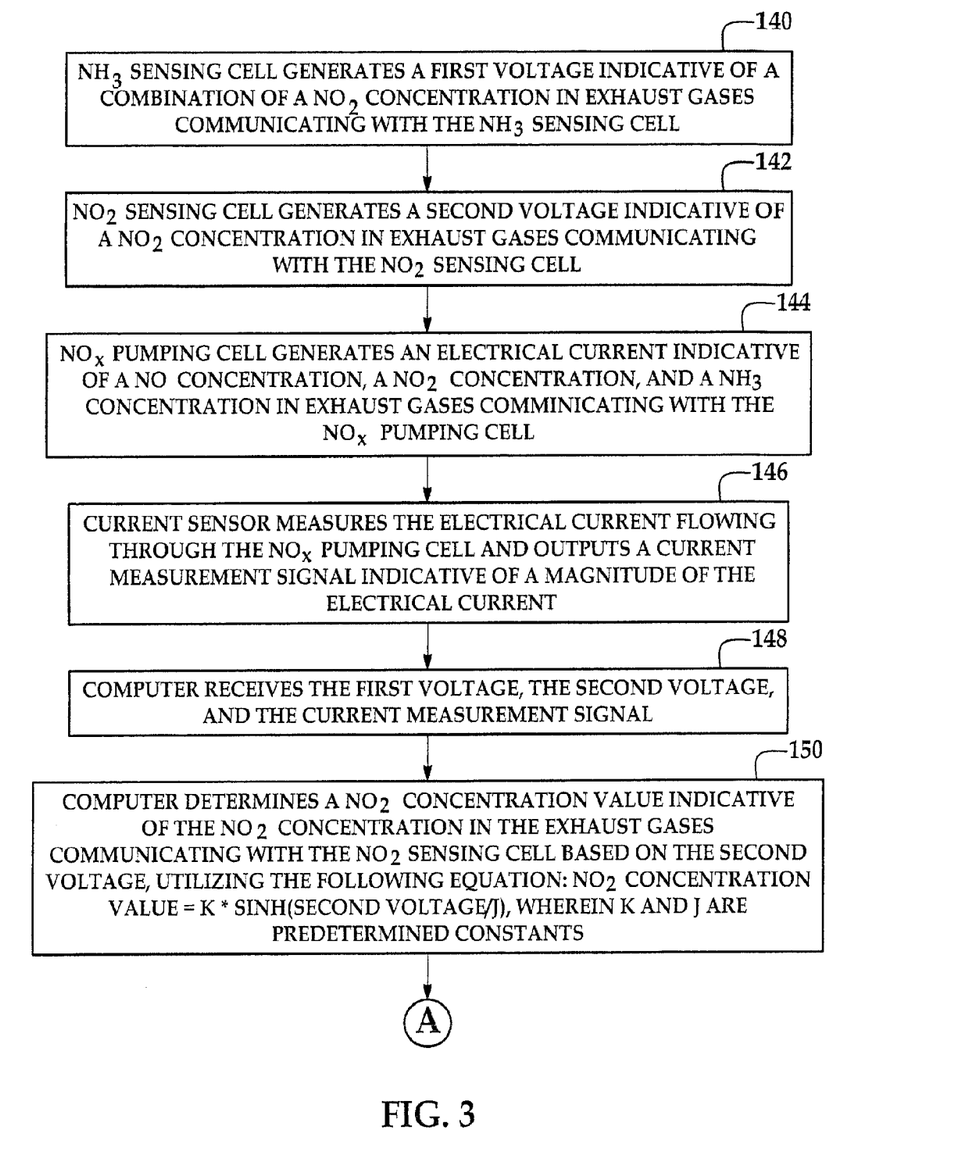
FIGS. 3 and 4 are flowcharts of a method for determining concentrations of exhaust gas constituents in accordance with another exemplary embodiment.
Figure 4:
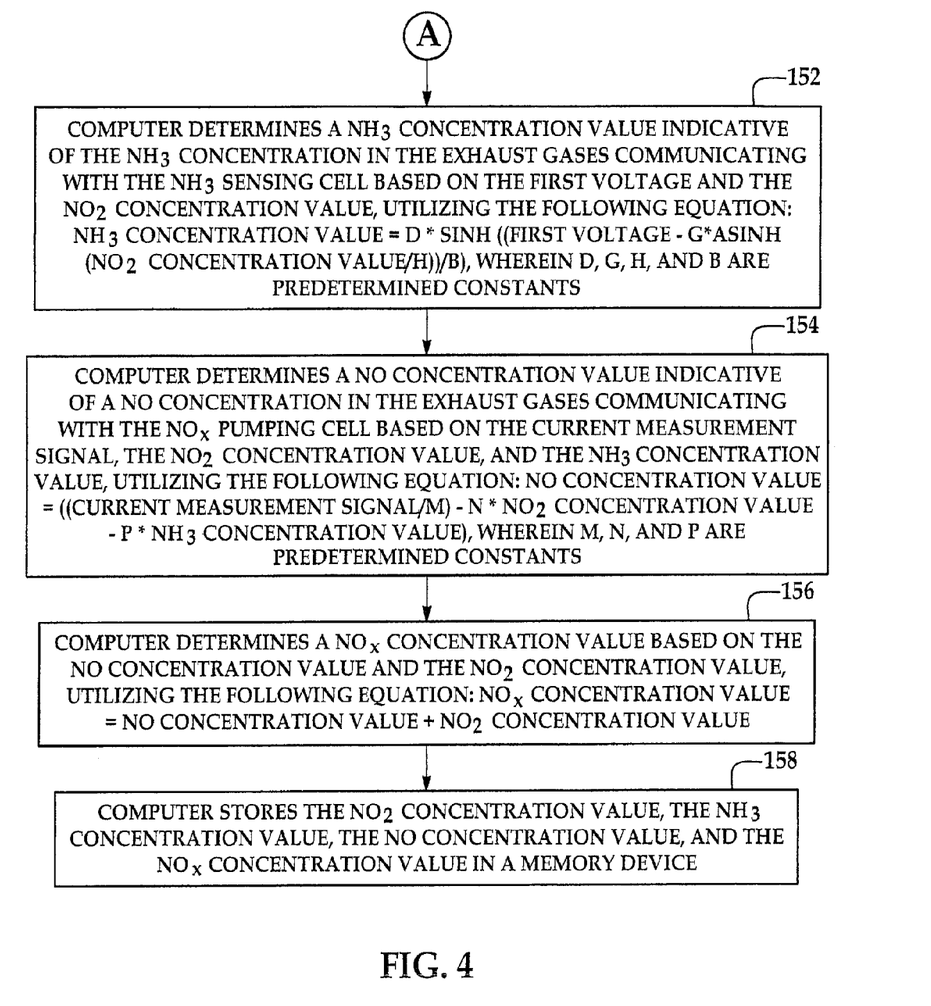

Referring to FIGS. 3-4, a flowchart of a method for determining concentrations of exhaust gas constituents in accordance with another exemplary embodiment will now be explained.

At step 140, the $NH_3$ sensing cell 82 generates a first voltage indicative of a combination of a $NH_3$ concentration and a $NO_2$ concentration in exhaust gases communicating with the $NH_3$ sensing cell 82.

At step 142, the $NO_2$ sensing cell 84 generates a second voltage indicative of a $NO_2$ concentration in exhaust gases communicating with the $NO_2$ sensing cell 84.

At step 144, the $NO_x$ pumping cell 113 generates an electrical current indicative of combination of a NO concentration, a $NO_2$ concentration, and a $NH_3$ concentration in exhaust gases communicating with the $NO_x$ pumping cell 113.

At step 146, the current sensor 48 measures the electrical current flowing through the $NO_x$ pumping cell 113 and outputs a current measurement signal indicative of a magnitude of the electrical current.

At step 148, the computer 42 receives the first voltage, the second voltage, and the current measurement signal.

At step 150, the computer 42 determines a $NO_2$ concentration value indicative of the $NO_2$ concentration in the exhaust gases communicating with the $NO_2$ sensing cell based on the second voltage, utilizing the following equation: $NO_2$ concentration value=K*SIN H(second voltage/J), wherein K and J are predetermined constants.

At step 152, the computer 42 determines a $NH_3$ concentration value indicative of the $NH_3$ concentration in the exhaust gases communicating with the $NH_3$ sensing cell 82 based on the first voltage and the $NO_2$ concentration value, utilizing the following equation:

$NH_3$ concentration value=D*SIN H((first voltage–G*ASIN H($NO_2$ concentration value/H))/B), wherein D, G, H, and B are predetermined constants.

At step 154, the computer 42 determines a NO concentration value indicative of a NO concentration in the exhaust gases communicating with the $NO_x$ pumping cell 113 based on the current measurement signal, the $NO_2$ concentration value, and the $NH_3$ concentration value, utilizing the following equation:

NO concentration value=((current measurement signal/M)–N*$NO_2$ concentration value–P*$NH_3$ concentration value), wherein M, N, and P are predetermined constants.

At step 156, the computer 42 determines a $NO_x$ concentration value based on the NO concentration value and the $NO_2$ concentration value, utilizing the following equation: $NO_x$ concentration value=NO concentration value+$NO_2$ concentration value.

At step 158, the computer 42 stores the $NO_2$ concentration value, the $NH_3$ concentration value, the NO concentration value, and the $NO_x$ concentration value in a memory device 43, which may be an internal memory device of the computer 42 or an external memory device to the computer 40.

Figure 5:
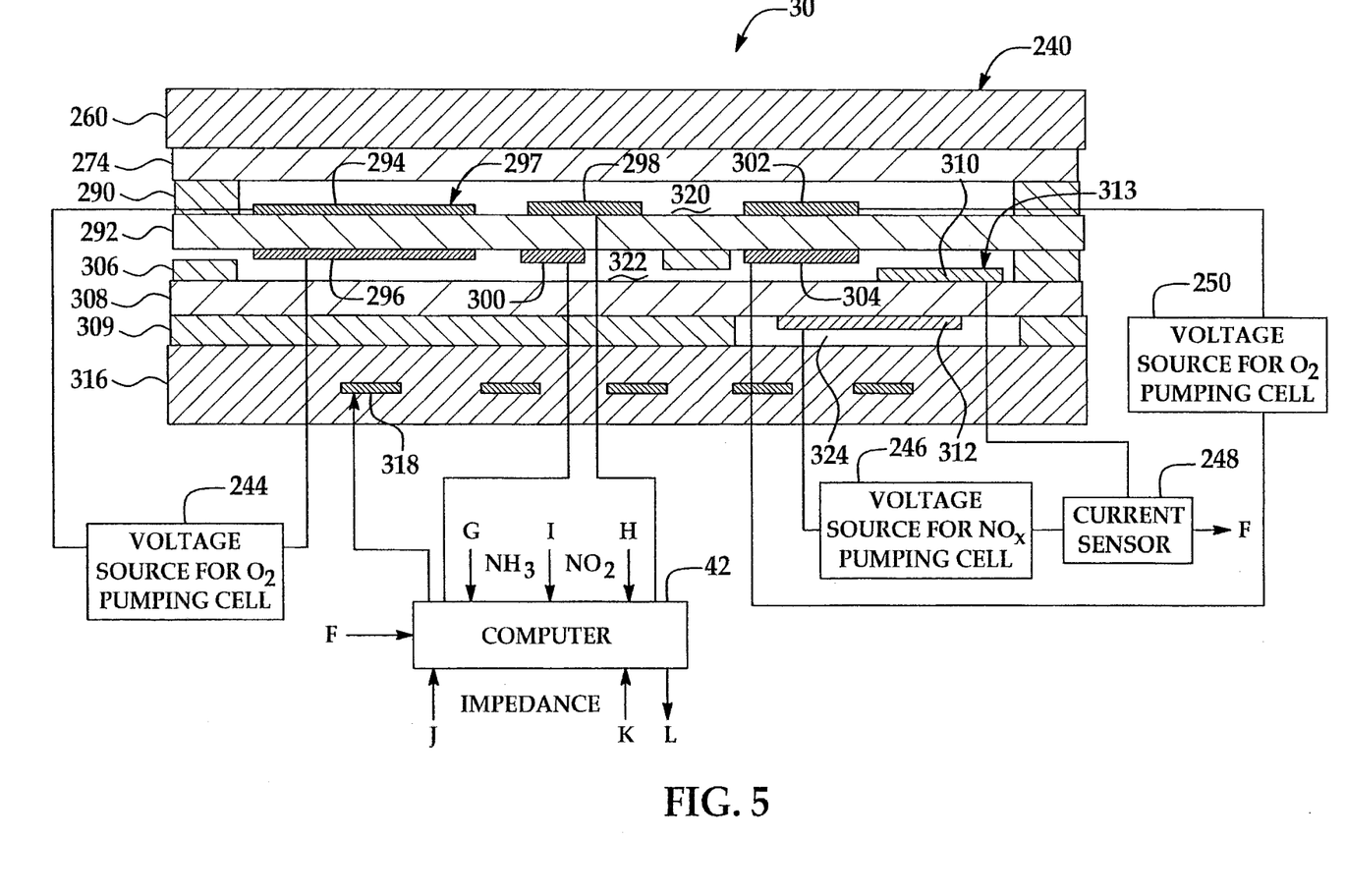
FIG. 5 is a schematic of a first exhaust gas sensor utilized in the second exhaust gas sensing system of FIG. 1.
Figure 6:
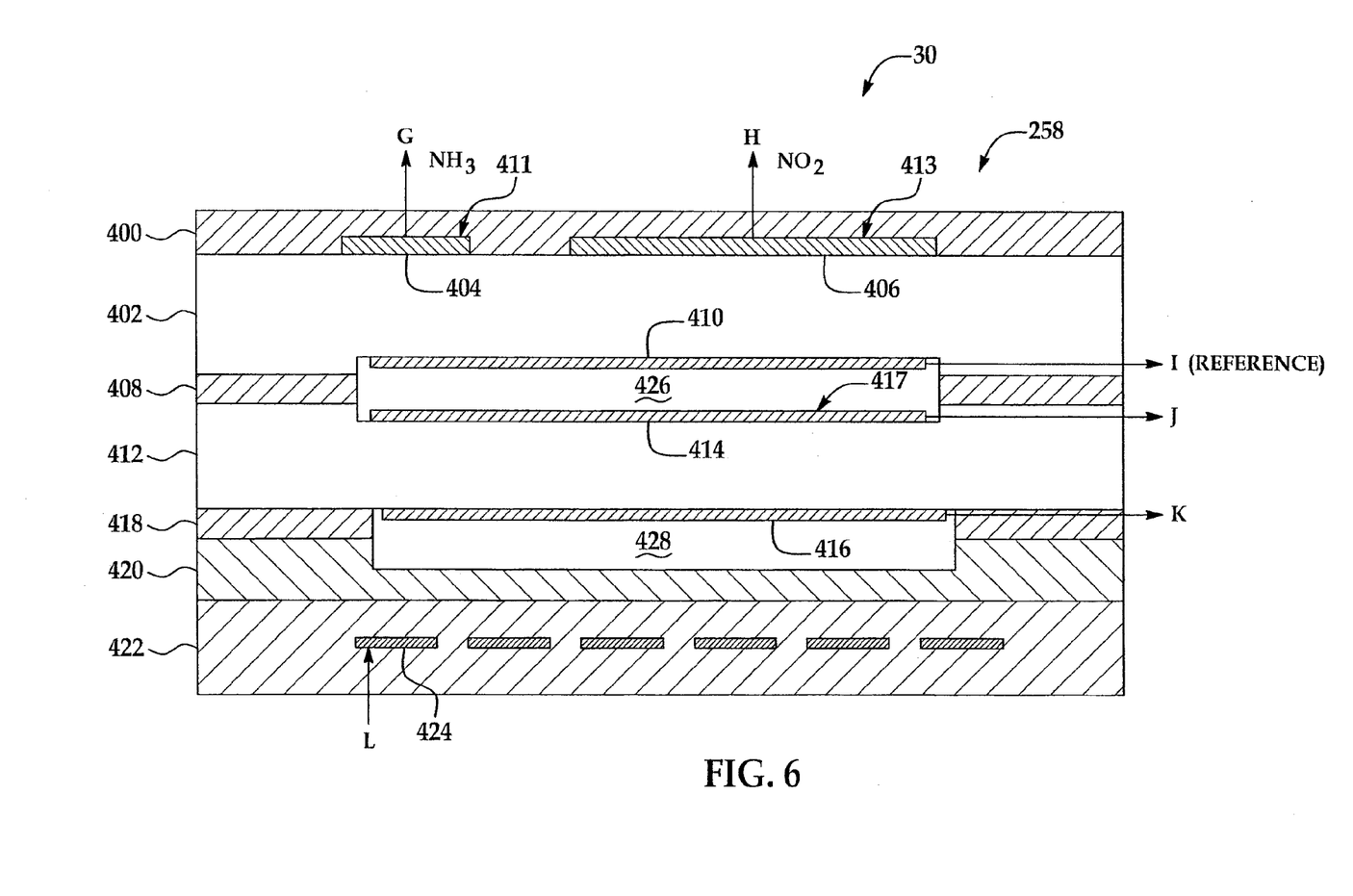
FIG. 6 is a schematic of a second exhaust gas sensor utilized in the second exhaust gas sensing system of FIG. 1.

Referring to FIGS. 5 and 6, the exhaust gas sensing system 30 can be utilized instead of the exhaust gas sensing system 28 to determine concentrations of $NO_2$, $NH_3$, NO, and $NO_x$ in the exhaust gases. The exhaust gas sensing system 30 includes an exhaust gas sensor 240, the computer 42, a voltage source 244, a voltage source 246, a current sensor 248, a voltage source 250, and an exhaust gas sensor 258.

The exhaust gas sensor 240 communicates with the exhaust gases in the exhaust pipe 26 and is configured to generate signals that are indicative of a $NO_x$ concentration in the exhaust gases. The exhaust gas sensor 240 includes a porous protection layer 260, a zirconia layer 274, an alumina layer 290, a zirconia layer 292, pump electrodes 294, 296, an $O_2$ sensing electrode 300, a reference electrode 298, pump electrodes 302, 304, an alumina layer 306, a zirconia layer 308, a $NO_x$ sensing electrode 310, a reference electrode 312, alumina layers 309, 316, and a heater coil 318.

The porous protection layer 260 is configured to protect the zirconia layer 274. In one exemplary embodiment, the porous protection layer 260 is constructed from porous alumina. As shown, the layer 260 is disposed at least in part on a first side of the zirconia layer 274. In one exemplary embodiment, the zirconia layer 274 is an oxide ion conducting solid electrolyte constructed of partially yttria-doped zirconia.

The alumina layer 290 is disposed between a second side of the zirconia layer 274 and a first side of the zirconia layer 292. A chamber 320 is formed in the alumina layer 290, which is communicated with ambient air by an air duct running through the sensing element body.

The pumping electrode 294 is disposed on a first side of the zirconia layer 292 and the pumping electrode 296 is disposed on a second side of the zirconia layer 292 proximate to the pumping electrode 294. The pumping electrodes 294, 296 are further electrically coupled to the voltage source 244. In one exemplary embodiment, the pumping electrodes 294, 296 are constructed of a Pt—Au alloy.

The combination of the voltage source 244, the electrodes 294, 296 and the zirconia layer 292 comprise an electrochemical pumping cell 297. The pumping cell 296 reduces an amount of oxygen in a first portion of the chamber 322 below a first predetermined oxygen concentration level.

The $O_2$ sensing electrode 298 is disposed on the first side of the zirconia layer 292 and the oxygen sensing electrode 300 is disposed on a second side of the zirconia layer 292 proximate to the $O_2$ reference electrode 298. The $O_2$ sensing electrode 300 and the reference electrode 298 are further electrically coupled to the computer 42. In one exemplary embodiment, the $O_2$ sensing electrode 300 and the reference electrode 298 are constructed of Pt. A voltage generated between the electrodes 298, 300 is indicative of an oxygen concentration in the chamber 322. The computer 42 measures the voltage between the electrodes 298, 300, indicative of the oxygen concentration, to regulate a voltage output by the voltage source 244 to maintain a concentration of oxygen in a portion of the chamber 322 below a second predetermined oxygen concentration level.

The pumping electrode 302 is disposed on a first side of the zirconia layer 292 and the pumping electrode 304 is disposed on a second side of the zirconia layer 292 proximate to the pumping electrode 302. The pumping electrodes 302, 304 are further electrically coupled to the voltage source 250. In one exemplary embodiment, the pumping electrodes 302, 304 are constructed of an Pt—Au alloy. The combination of the voltage source 250, the electrodes 302, 304 and the zirconia layer 292 comprise an electrochemical pumping cell 297. The pumping cell 297 reduces an amount of oxygen in a second portion of the chamber 322 below a second predetermined oxygen concentration level.

The alumina layer 306 is disposed between the second side of the zirconia layer 292 and a first side of the zirconia layer 308. A chamber 322 is formed in the alumina layer 306 and fluidly communicates with engine exhaust with a gas-diffusion-limiting aperture extending through a portion of the alumina layer 306. A second gas-diffusion-limiting aperture is set between the electrode 300 and the electrode 304 to limit the gas diffusion within the chamber 322 between the electrodes 300 and 304.

The zirconia layer 308 is disposed between the second side of the alumina layer 306 and a first side of the alumina layer 309. A second side of the alumina layer 309 is disposed on a first side of the alumina layer 316. A chamber 324 is formed in the alumina layer 309. Further, in one exemplary embodiment, the zirconia layer 308 is an oxide ion conducting solid electrolyte constructed of partially yttria-doped zirconia.

The $NO_x$ sensing electrode 310 is disposed on the first side of the zirconia layer 308 fluidly communicates with exhaust gases in the chamber 322. In one exemplary embodiment, the $NO_x$ sensing electrode 310 is constructed of a Pt—Rh alloy. The reference electrode 312 is disposed on the second side of the zirconia layer 308 proximate to the $NO_x$ sensing electrode 310 and fluidly communicates with exhaust gases in the chamber 324. In one exemplary embodiment, the reference electrode 312 is constructed of Pt—Au alloy. The electrodes 310, 312 are electrically coupled to a series combination of the voltage source 246 and a current sensor 248.

The combination of the voltage source 246, the electrodes 310, 312 and the zirconia layer 308 comprise a $NO_x$ electrochemical pumping cell 313 that generates a current indicative of a $NO_x$ concentration in the chamber 322. The current sensor 248 outputs a signal indicative of an amount of electrical current flowing between the electrodes 310, 312, that is received by the computer 42.

The heater coil 318 is disposed in the alumina layer 316. The heater coil 318 is configured to maintain the exhaust gas sensor 240 within a predetermined temperature range in response to a control signal from the computer 42.

Referring to FIG. 6, the exhaust gas sensor 258 will now be explained. The exhaust gas sensor 258 communicates with the exhaust gases in the exhaust pipe 26 and is configured to generate signals indicative of a $NH_3$ concentration and a $NO_2$ concentration, and a temperature of the exhaust gas sensor 258.

The exhaust gas sensor 258 includes a porous protection layer 400, a zirconia layer 402, a $NH_3$ sensing electrode 404, a $NO_2$ sensing electrode 406, a porous alumina layer 408, a reference electrode 410, a zirconia layer 412, reference electrodes 414, 416, a porous alumina layer 418, alumina layers 420, 422, and a heater coil 424.

The porous protection layer 400 is configured to allow exhaust gases to diffuse therethrough to contact the $NH_3$ sensing electrode 404 and the $NO_2$ sensing electrode 406. As shown, the layer 400 is disposed at least in part on a first side of the zirconia layer 402. In one exemplary embodiment, the porous protection layer 400 is constructed from porous alumina, and the zirconia layer 402 is an oxide ion conducting solid electrolyte constructed of partially yttria-doped zirconia. Further, the $NH_3$ sensing electrode 404 is constructed of $BiVO_4$ doped with 0-20 mole % of MgO, 0-10 mole % of $B2O_3$, 0-10 mole % of SrO and the $NO_2$ sensing electrode is constructed of $BaFe_{12}O_{19}$ doped with 0-20 mole % of BaO, 0-20 mole % of (MgO, NiO, ZnO). The reference electrode 410 is disposed on a second side of the zirconia layer 410. In one exemplary embodiment, the reference electrode 410 is constructed of a Pt alloy.

The combination of the $NH_3$ sensing electrode 404, the zirconia layer 402, and the reference electrode 410 form a $NH_3$ sensing cell 411 (e.g., $NH_3$ sensing Nernst cell) that generates a voltage indicative of a $NH_3$ concentration communicating with the $NH_3$ sensing electrode 404, that is received by the computer 42.

The combination of the $NO_2$ sensing electrode 406, the zirconia layer 402, and the reference electrode 410 form a $NO_2$ sensing cell 413 (e.g., $NO_2$ sensing Nernst cell) that generates a voltage indicative of a $NO_2$ concentration communicating with the $NO_2$ sensing electrode 406, that is received by the computer 42.

A portion of a second side of the zirconia layer 402 is disposed on a first side of the alumina layer 408. A chamber 426 is formed in the alumina layer 408 and adjacent portions of the zirconia layer 402 and the zirconia layer 412. At least a peripheral portion of the alumina layer 408 is porous which allows exhaust gases to diffuse therethrough into the chamber 426. A reference electrode 414 is disposed on a first side of the zirconia layer 412 and communicates with exhaust gases in the chamber 426.

A portion of a second side of the alumina layer 408 is disposed on a first side of the zirconia layer 412. A portion of a second side of the zirconia layer 412 is disposed on a first side of the alumina layer 418. A chamber 428 is formed in the alumina layer 418 and a portion of the alumina layer 420. The reference electrode 416 is disposed on the second side of the zirconia layer 412. The chamber 428 communicates with the engine exhaust gases via a portion of the alumina layer 418 being constructed of gas porous alumina.

The combination of the electrodes 414, 416 and the zirconia layer 412 comprise a temperature sensor 417. In particular, an impedance between the electrodes 414, 416 is indicative of a temperature of the exhaust gas sensor 258 and a temperature of exhaust gases communicating with the exhaust gas sensor 258. The computer 42 can measure the impedance between the electrodes 414, 416 and determine a temperature value indicative of the temperature of the sensor 258, based on the impedance.

A second side of the alumina layer 420 is disposed on the alumina layer 422. The heater coil 424 is disposed in the alumina layer 420. The heater coil 424 is configured to maintain the exhaust gas sensor 258 within a predetermined temperature range in response to a control signal from the computer 42.

In an alternative embodiment, the computer 42 is configured to calculate a $NO_2$ concentration value, a $NH_3$ concentration value, a NO concentration value, and a $NO_x$ concentration value indicative of: a $NO_2$ concentration, a $NH_3$ concentration, a NO concentration, and a $NO_x$ concentration, respectively, in exhaust gases communicating with the exhaust gas sensors 240, 258 based on signals from the sensors 240, 258, and the current sensor 248. As shown, the computer 42 is electrically coupled to the voltage source 244, the $NH_3$ sensing electrode 404, the reference electrode 410, the $NO_2$ sensing electrode 406, the current sensor 248, and the heater coil 424.

Further, it should be noted that the exhaust gas sensing system 30 can be utilized to implement the method described in the flowchart of FIGS. 3 and 4, instead of the exhaust gas sensing system 28, utilizing the signals from the sensors 240, 258, and the current sensor 248.

The exhaust gas sensing systems and the method for determining concentrations of exhaust gas constituents provide a substantial advantage over other systems and methods. In particular, the exhaust gas sensing systems and the method provide a technical effect of accurately determining $NO_x$, $NO_2$, $NH_3$, and NO concentrations in exhaust gases.

While embodiments of the invention are described with reference to the exemplary embodiments, it will be understood by those skilled in the art that various changes may be made and equivalents may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling within the scope of the intended claims. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

What is claimed is:

1. An exhaust gas sensing system, comprising:
    a $NH_3$ sensing cell configured to generate a first voltage indicative of a combination of a $NH_3$ concentration and a $NO_2$ concentration in exhaust gases communicating with the $NH_3$ sensing cell;
    a $NO_2$ sensing cell configured to generate a second voltage indicative of a $NO_2$ concentration in exhaust gases communicating with the $NO_2$ sensing cell;
    a $NO_x$ pumping cell electrically coupled to a voltage source that is configured to generate an electrical current through the $NO_x$ pumping cell, the magnitude of said electrical current indicative of combination of a NO concentration, a $NO_2$ concentration, and a $NH_3$ concentration in exhaust gases communicating with the $NO_x$ pumping cell;
    a current sensor configured to measure the electrical current flowing through the $NO_x$ pumping cell and to output a current measurement signal indicative of a magnitude of the electrical current;
    a computer configured to receive the first voltage, the second voltage, and the current measurement signal, the computer further configured to determine a $NO_2$ concentration value indicative of the $NO_2$ concentration in the exhaust gases communicating with the $NO_2$ sensing cell based on the second voltage;
    the computer further configured to determine a $NH_3$ concentration value indicative of the $NH_3$ concentration in the exhaust gases communicating with the $NH_3$ sensing cell based on the first voltage and the $NO_2$ concentration value;
    the computer further configured to determine a NO concentration value indicative of a NO concentration in the exhaust gases communicating with the $NO_x$ pumping cell based on the current measurement signal, the $NO_2$ concentration value, and the $NH_3$ concentration value;
    the computer further configured to determine a $NO_x$ concentration value based on the NO concentration value and the $NO_2$ concentration value; and
    the computer further configured to store the $NO_2$ concentration value, the $NH_3$ concentration value, the NO concentration value, and the $NO_x$ concentration value in a memory device.

2. The exhaust gas sensing system of claim 1, wherein the $NH_3$ sensing cell and the $NO_2$ sensing cell are disposed in a first exhaust gas sensor and the $NO_x$ pumping cell is disposed in a second exhaust gas sensor that is not a part of the first exhaust gas sensor.

3. The exhaust gas sensing system of claim 1, wherein the $NH_3$ sensing cell, the $NO_2$ sensing cell, and the $NO_x$ pumping cell are disposed in an exhaust gas sensor.

4. A method for determining concentrations of exhaust gas constituents, comprising:
    generating a first voltage utilizing a $NH_3$ sensing cell that is indicative of a combination of a $NH_3$ concentration and a $NO_2$ concentration in exhaust gases communicating with the $NH_3$ sensing cell;
    generating a second voltage utilizing a $NO_2$ sensing cell that is indicative of a $NO_2$ concentration in exhaust gases communicating with the $NO_2$ sensing cell;
    generating an electrical current utilizing a voltage source that is electrically coupled to a $NO_x$ pumping cell wherein the magnitude of the electrical current is indicative of combination of a NO concentration, a $NO_2$ concentration, and a $NH_3$ concentration in exhaust gases communicating with the $NO_x$ pumping cell;
    measuring the electrical current flowing through the NOx pumping cell utilizing a current sensor and outputting a current measurement signal from the current sensor indicative of a magnitude of the electrical current;
    receiving the first voltage, the second voltage, and the current measurement signal at a computer;
    determining a $NO_2$ concentration value indicative of the $NO_2$ concentration in the exhaust gases communicating with the $NO_2$ sensing cell based on the second voltage, utilizing the computer;
    determining a $NH_3$ concentration value indicative of the $NH_3$ concentration in the exhaust gases communicating with the $NH_3$ sensing cell based on the first voltage and the $NO_2$ concentration value, utilizing the computer;
    determining a NO concentration value indicative of a NO concentration in the exhaust gases communicating with the $NO_x$ pumping cell based on the current measurement signal, the $NO_2$ concentration value, and the $NH_3$ concentration value, utilizing the computer;
    determining a $NO_x$ concentration value based on the NO concentration value and the $NO_2$ concentration value, utilizing the computer; and
    storing the $NO_2$ concentration value, the $NH_3$ concentration value, the NO concentration value, and the $NO_x$ concentration value in a memory device, utilizing the computer.

* * * * *